(12) United States Patent
Isrow et al.

(10) Patent No.: US 11,771,717 B2
(45) Date of Patent: Oct. 3, 2023

(54) APPLICATIONS OF PAIR-PRODUCTION FOR IMPROVED RADIOTHERAPY

(71) Applicant: Henry Ford Health System, Detroit, MI (US)

(72) Inventors: Derek M. Isrow, Pinecrest, FL (US); Stephen L. Brown, LaSalle (CA); Jae Ho Kim, Irvine, CA (US); Indrin J. Chetty, Canton, MI (US); Panagiotis Tsiamas, Houston, TX (US)

(73) Assignee: Henry Ford Health System, Detroit, MI (US)

( * ) Notice: Subject to any disclaimer, the term of this patent is extended or adjusted under 35 U.S.C. 154(b) by 873 days.

(21) Appl. No.: 16/486,367

(22) PCT Filed: Feb. 15, 2018

(86) PCT No.: PCT/US2018/018380
§ 371 (c)(1),
(2) Date: Aug. 15, 2019

(87) PCT Pub. No.: WO2018/152332
PCT Pub. Date: Aug. 23, 2018

(65) Prior Publication Data
US 2020/0001111 A1    Jan. 2, 2020

Related U.S. Application Data

(60) Provisional application No. 62/459,283, filed on Feb. 15, 2017.

(51) Int. Cl.
| | | |
|---|---|---|
| *A61K 33/24* | (2019.01) | |
| *A61P 35/00* | (2006.01) | |
| *A61K 33/243* | (2019.01) | |
| *A61K 31/282* | (2006.01) | |
| *A61K 33/00* | (2006.01) | |
| *A61N 5/10* | (2006.01) | |
| *A61K 33/242* | (2019.01) | |

(52) U.S. Cl.
CPC ............ *A61K 33/24* (2013.01); *A61K 31/282* (2013.01); *A61K 33/00* (2013.01); *A61K 33/242* (2019.01); *A61K 33/243* (2019.01); *A61N 5/10* (2013.01); *A61P 35/00* (2018.01); A61N 2005/1091 (2013.01); A61N 2005/1098 (2013.01)

(58) Field of Classification Search
CPC .... A61K 33/24; A61K 33/242; A61K 31/282; A61N 5/10; A61P 35/00
See application file for complete search history.

(56) References Cited

U.S. PATENT DOCUMENTS

| | | |
|---|---|---|
| 2004/0181114 A1 | 9/2004 | Hanfield et al. |
| 2010/0173885 A1 | 7/2010 | Therrian et al. |
| 2014/0235923 A1 | 8/2014 | McNutt et al. |
| 2016/0015639 A1 | 1/2016 | Geschwind et al. |

OTHER PUBLICATIONS

PCT International Search Report, PCT/US2018/018380, dated Apr. 27, 2018 (3 pages).
Tsiamas, P., et al., "Dosimetric Evaluation and Beam Characterization of PAIR Production Enhanced Radiotherapy (PPER) With The Use of Organometallics," Physics In Medicine & Biology, vol. 64, Apr. 4, 2019.

*Primary Examiner* — Kevin E Weddington

(57) ABSTRACT

The present invention relates to the treatment of cancer by irradiation by high energy photons, wherein the cancer has been infused with a heavy metal. The invention further relates to the use of pair-production for increased cancer cell destruction.

7 Claims, 10 Drawing Sheets

APPLICATIONS OF PAIR-PRODUCTION FOR IMPROVED RADIOTHERAPY

CROSS-REFERENCE TO RELATED APPLICATION

This application claims priority to PCT International Application No. PCT/US2018/018380, filed Feb. 15, 2018, which claims the benefit of, and priority to, U.S. Provisional Application Ser. No. 62/459,283, filed on Feb. 15, 2017. The entire contents of these applications are incorporated herein by reference in their entirety.

TECHNICAL FIELD

The present invention relates to the treatment of cancer by irradiation using high energy photons, wherein the cancer has been administered, either through blood supply or direct injection, with a heavy organometallic compound. The invention further relates to the use of pair-production for increased cancer cell destruction.

BACKGROUND

Radiation therapy or radiotherapy (RT, RTx, or XRT), is therapy using ionizing radiation, generally as part of cancer treatment to control or kill hyper-proliferative cells, for example cancer cells. Radiation therapy uses ionizing radiation. Radiation therapy may be curative in a number of types of cancer if they are localized to one area of the body. It may also be used as part of adjuvant therapy, to prevent tumor recurrence after surgery to remove a primary malignant tumor. Radiation therapy is synergistic with chemotherapy, and has been used before, during, and after chemotherapy in susceptible cancers.

Radiotherapy is part of the treatment regimen for a large percentage of cancer diagnoses. Increasing the effectiveness of this radiotherapy to improve tumor control and clinical outcomes is essential. Many compounds have been tested over the years to enhance radiotherapeutic effects on cancerous tissues with few proving successful. One of the most notable is cisplatin, an organometallic chemotherapy with known toxic effects. This drug has shown synergistic interaction with radiotherapy to improve tumor control and outcomes, though cisplatin itself causes significant morbidity and mortality. Nanoparticles of gold and other metals have also shown promise in this respect, however most work done demonstrated radiosensitization to be greatest at energies of approximately 250 kV or less, significantly lower than that used in routine clinical X-ray therapy.

Energy is known to interact with matter in 3 main ways, though there are other minor mechanisms. The photoelectric effect is the foundation of diagnostic radiology and dominates at lower energy photon interactions of approximately 100 kV or less. Its probabilistic cross section is proportional to $Z^3$ which is why calcified bone is resolved better than soft tissue. This electron ejection mechanism is thought to be the primary process by which nanoparticles enhance radiation therapy at lower energies. Compton scattering is the prominent interaction of modern clinical radiation therapy and typically occurs from 100 kV up to 3 MV energies. It involves the photon interacting with an orbital electron resulting in the redirection of a lower energy photon and ejection of a fast moving energetic electron. This process is not dependent on the Z of incident material. As photon energy increases, the third interaction becomes more probable, pair-production. This mechanism requires at least 1.022 MeV photons that interact with the nuclear field of an atom to create a positron-electron pair (higher energy photons generate positron-electron pairs with greater than rest-mass energies). These pairs then seek out their counter parts (positrons to electrons and vice versa) and annihilate resulting in 2 photons traveling nearly 180 degrees apart at energies of at least 511 keV. This process is dependent on the $Z^2$ of the material.

Pair-production which has the potential to enhance radiotherapy has not been adequately studied for use in oncology. Radiation dose is a measure of energy deposited by the high energy photon as it passes through tissue. Most radiation oncology clinics currently use linear accelerators at 6 MV, however many machines are capable of utilizing 18 MV which is sufficient for pair-production. If a high Z metal compound is given at some time before irradiation with these high energy X-rays, an increased number of photons will interact with the metal atoms in the cancerous tissue via pair-production, thus increasing dose to the local environment while still giving the same prescribed amount of radiation. This pair-production will result in annihilation photons and these can be imaged and counted to give data on dose enhancement. Tumor environments have been shown to preferentially accumulate several metal compounds and particles due to their leaky vasculature and, potentially, due to their acidic environments, and these properties can be used to enhance the radiotherapeutic ratio between normal and malignant tissue. Similarly, metal drugs can be developed with low toxicity profiles and modified to preferentially accumulate in cancerous tissues via targeting methods such as antibodies, peptides, and other chemical moieties. It is this possibility of utilizing non-toxic metal compounds rather than traditional platinum based therapies with significant toxicity profiles that is most exciting and opens up a new world of metal based cancer therapies modified to produce useful chemistries as well as pair-production radiosensitization.

Pair production is one of the three principal ways in which high-energy photons are absorbed in matter. Routine radiation therapy does not typically exploit the process of pair production, because the advantages of this approach have not been recognized. We demonstrate, for the first time, that for pair production to occur and to cause enhanced cytotoxicity, unimolecular or clustered heavy metal organometallic compounds need to be delivered to target cancer cells.

SUMMARY

Figure 1A:
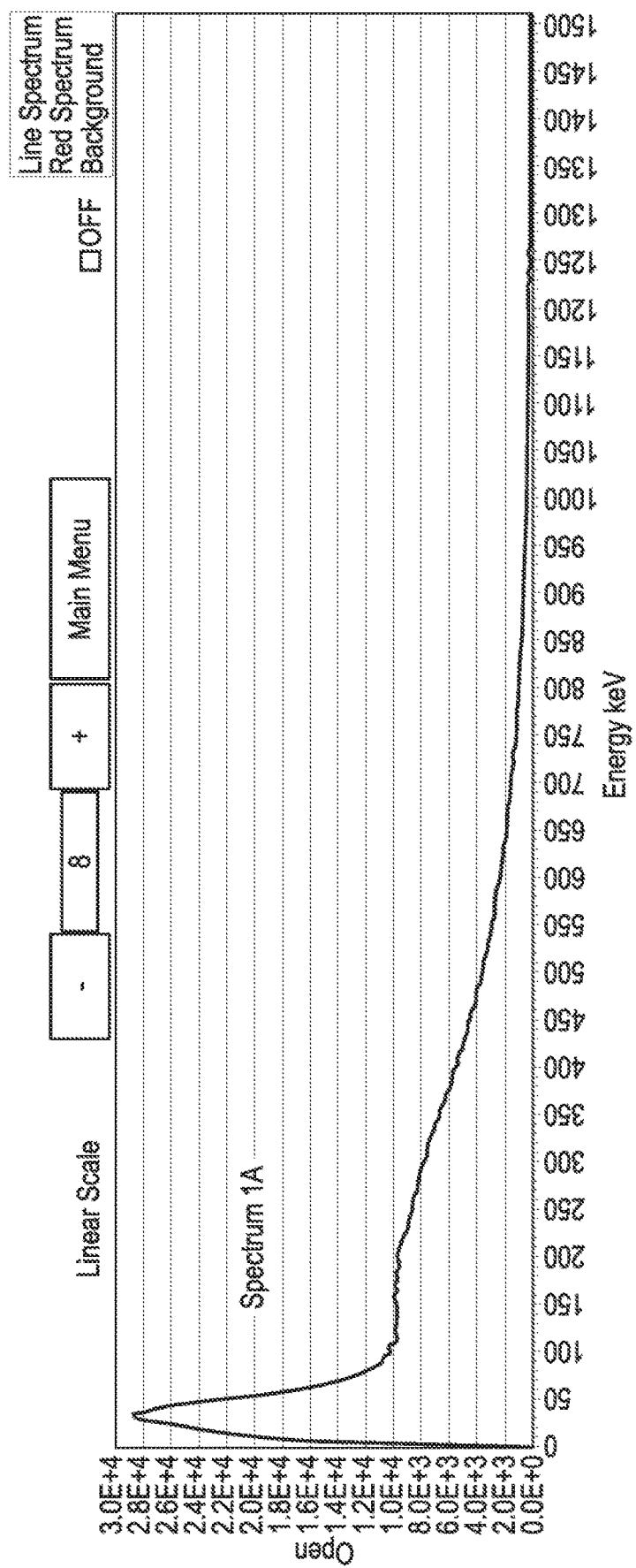
FIG. 1A is a graph of the output of a scintillation detector showing no increase in the emission of photons around 511 keV, suggesting no pair-production as a 50 mL water sample is irradiated with 18 MV photons.

The present invention includes an improvement of radiation therapy effectiveness. Radiation is targeted on cancerous tissue geometrically. The effectiveness of radiation therapy is dictated by the intrinsic radiation sensitivity of cancer cells. An improvement in the intrinsic radiation sensitivity of cancer cells can increase the effectiveness of radiation therapy.

Chemotherapeutic agents that contain heavy metals are routinely used to treat many solid cancers including head & neck, lung, GYN, etc. The timing of heavy metal chemotherapies or second-generation metal-based drugs with improved toxicity profiles compared to platinum based chemotherapies has not been optimized with respect to timing of radiation therapy previously. Current practice is based on patient or clinic convenience. We demonstrate that the timing between radiation exposure and administration of heavy metal compounds is critically important when high energy photons are used. Metal drugs should be administered before radiation therapy so that their concentration in tumor tissues is maximum at the time of radiation exposure. The optimum administration of metal based radioenhancers may allow patients to receive overall lower radiation doses with similar effect to currently prescribed regimens, or still receive the current standard prescription doses with higher probability of cure.

Current state-of-the-art radiation therapy routinely utilizes 6 MV photon energy except for extraordinarily large patients in which increased penetration of energetic photons are needed. 6 MV photons interact with human tissues via either photoelectric or Compton effects. The advantage, not previously recognized, of routinely using higher energy photons with unimolecular and clustered heavy metal organometallic compounds is that pair-production interaction increases with increasing photon energy and Z-value of the matter. Thus, increased interactions with tumor tissues occurs if high energy photons are used and metal compounds are present. Consequently, either the same amount of radiation can produce a larger effect, or less radiation can be used to achieve the same effect. The timing of metal administration and irradiation will be crucial as metal concentration will affect the increased amount of absorbed radiation. The phenomenon of pair-production also leads to positron-electron annihilation and characteristic x-ray photon production which can be monitored with appropriate technology similar to PET scanners. The annihilation photons could be used to image tumors during treatment, calculate actual dose to tumors, and analyze tumor response.

There is significant potential to commercialize the invention of exploiting high energy photons with optimum-timed metal delivery. Although current state-of-the-art clinical linear accelerators are capable of producing high energy photons and metal compounds are routinely used to treat cancers, there are at least three advances with commercial potential. First, new metal based compounds can be developed with low levels of toxicity and high tumor-specific uptake, and these can be used during radiation therapy as radioenhancers. These compounds can be targeted via molecular markers or tailored to produce chemical reactions inside tumor cells resulting in improved cancer outcomes. Even currently used chemotherapies such as cisplatin and carboplatin could be implemented in this manner if given at appropriate times before radiation therapy. Secondly, linear accelerators can be developed to produce even higher energy photons which would result in enhanced pair-production interactions and higher dose to metal containing tumors while sparing normal tissues. Thirdly, linear accelerators could be developed with on-board imagers designed to visualize pair-production annihilation photons, similar to PET-scanners, and this would provide image guidance, tumor response, and tumor dose information.

In one aspect, the invention includes a method of treating cancer in a patient, wherein the patient is a mammal, comprising the steps of:
  a. administering to the patient a pharmaceutically acceptable composition comprising a heavy metal organometallic compound;
  b. allowing a time interval to pass; and
  c. irradiating the area of the patient previously identified as the location of the cancer with high energy photons sufficient to induce positron-electron pair production.

DETAILED DESCRIPTION

Definitions

As used herein, the term "pair-production" is the formation or materialization of an electron-positron pair from a pulse of electromagnetic energy traveling through matter, usually in the vicinity of an atomic nucleus.

As used herein, the term "heavy metal" is used interchangeably with the term "high Z metal" and refers to any metallic chemical element that has a relatively high density or atomic number (Z). Examples of heavy metals are, but are not limited to, tungsten (W), mercury (Hg), gold (Au), platinum (Pt), cadmium (Cd), arsenic (As), chromium (Cr), thallium (Tl), and lead (Pb).

As used herein, the term "linear particle accelerator" is interchangeable with the term "linear accelerator" and "linac" and refers to an instrument capable of delivering high-energy x-rays to a specific region of a patient's tumor.

A linear particle accelerator is the device most commonly used for external beam radiation treatments for patients with cancer, and is widely used to treat all parts/organs of the body.

As used herein, the term "heavy metal organometallic compound" refers to an organic chemical compound containing at least one bond between a carbon atom of the organic compound and a heavy metal atom. Unless specified otherwise, organometallic compounds referred to herein do not include polymeric or oligomeric compounds.

As used herein, the term "unimolecular heavy metal organometallic compounds" refers to heavy metal organometallic compounds that act as single entities and do not significantly interact or complex with each other.

As used herein, the term "clustered heavy metal organometallic compounds" refers to heavy metal organometallic compounds that further involve intermolecular bonding interactions between specific atoms of the compounds, such as metal-metal, coordination, or hydrogen bonding. Clustered heavy metal organometallic compounds consist of a finite number of individual compounds, such as a dimer or trimer, and are not polymeric in nature.

EMBODIMENTS OF THE INVENTION

The present disclosure provide a method for treating cancer, wherein high energy photons (for example, 18 MV or greater) delivered in conjunction with unimolecular and clustered heavy metal organometallic compounds, including but not limited to sodium phosphotungstate hydrate ($Na_3PW_{12}O_{40}*H_2O$), sodium tungstate dihydrate ($Na_2WO_6H_2$), and cisplatin ($PtCl_2N_2H_6$), enhance cell killing compared to cell killing by lower energy (for example, 6 MV photons) whether heavy metals are present or not. The enhanced cytotoxicity of high energy photons in the presence of heavy metals is a result of pair production.

High energy photons are routinely available from modern linear accelerators. Heavy metals are routinely used as a chemotherapeutic for the treatment of many cancers. What has not been recognized previously, and that we demonstrate for the first time is that the timing of administration of metal relative to radiation exposure is the critical step to exploit pair production to optimally kill cancer cells.

Nearly all linear accelerators in radiation oncology clinics treat patients with 6 MV photons. However, many are capable of much higher energies: 10, 15, 18, or even higher megavoltage photons. By utilizing the highest energies available in conjunction with either platinum based chemotherapies or novel heavy metal compounds given shortly before irradiation, patients will experience higher probability of cure due to the enhanced interaction of photons with metal atoms in tumors due to increased pair-production. The metals will need to be given at specified times before irradiation to ensure highest possible concentrations in tumor tissues leading to increased effectiveness of photon-matter interactions.

In one aspect, the invention includes a method of treating cancer in a patient, wherein the patient is a mammal, comprising the steps of:
 a. administering to the patient a pharmaceutically acceptable composition comprising a heavy metal organometallic compound;
 b. allowing a time interval to pass; and
 c. irradiating the area of the patient previously identified as the location of the cancer with high energy photons sufficient to induce positron-electron pair production.

In one embodiment of this aspect, the patient is a human. In another embodiment, the method includes treating a solid tumor in a patient. In a further embodiment, the treatment includes reducing the size of the tumor. In another further embodiment, the treatment includes killing cells of the tumor.

In another embodiment of this aspect, the heavy metal organometallic compound comprises one or more of tungsten, platinum, gold, mercury, cadmium, arsenic, chromium, thallium, and lead. In a further embodiment, the heavy metal organometallic compound comprises a metal having low toxicity. In still a further embodiment, the heavy metal organometallic compound comprises tungsten.

In one embodiment, the time interval is from 1 minute to 24 hours. In one embodiment, the time interval is from 5 minutes to 12 hours. In one embodiment, the time interval is from 10 minutes to 6 hours. In one embodiment, the time interval is from 20 minutes to 3 hours. In one embodiment, the time interval is from 20 minutes to 2 hours. In one embodiment, the time interval is from 30-90 minutes. In one embodiment, the time interval is from 45-75 minutes. In one embodiment, the time interval is from 50-70 minutes. In one embodiment, the time interval is from 55-65 minutes. For example, the time interval can be 1-5 minutes, 5-10 minutes, 10-15 minutes, 15-20 minutes, 20-25 minutes, 25-30 minutes, 30-40 minutes, 40-50 minutes, 50-60 minutes, 60-70 minutes, 70-80 minutes, 80-90 minutes, 90-100 minutes, 100-120 minutes, 120-150 minutes, 150-180 minutes, 180-210 minutes, 210-240 minutes, 240-270 minutes, or 270-300 minutes. As a further example, the time interval can be about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 1 hour, about 1.25 hours, about 1.5 hours, about 1.75 hours, about 2 hours, about 2.5 hours, about 3 hours, or about 4 hours.

In one embodiment, the high energy photons are greater than 10 MV. In a further embodiment, the high energy photons are greater than 18 MV. In another embodiment, the high energy photons are from 15 MV to 50 MV.

In one embodiment, the dose of high energy photons is from 2 to 20 Gr, for example 2 to 4 Gr, 4 to 6 Gr, 6 to 8 Gr, 8 to 10 Gr, 10 to 12 Gr, 12 to 14 Gr, 14 to 16 Gr, 16 to 18 Gr, or 18 to 20 Gr.

Uses and Methods of Use

Pharmaceutically Acceptable Compositions

In one aspect of the present invention, pharmaceutically acceptable compositions are provided, wherein these compositions comprise any of the compounds as described herein, and optionally comprise a pharmaceutically acceptable carrier, adjuvant or vehicle.

It will also be appreciated that certain compounds of the present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, edisylate (ethanedisulfonate), ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In one aspect, the invention includes a method of treating cancer in a patient, wherein the patient is a mammal. In one embodiment of this aspect, the patient is a human. In another embodiment, the method includes treating a solid tumor in a patient. In a further embodiment, the treatment includes reducing the size of the tumor. In another further embodiment, the treatment includes killing cells of the tumor.

In another embodiment of this aspect, the cancer is selected from the group consisting of Acute Lymphoblastic Leukemia (ALL), Acute Myeloid Leukemia (AML), Adrenocortical Carcinoma, Adult, Childhood Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Astrocytomas, Childhood (Brain Cancer), Atypical Teratoid/Rhabdoid Tumor, Childhood, Central Nervous System (Brain Cancer), Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Childhood Breast Cancer, Childhood Bronchial Tumors, Burkitt Lymphoma, Carcinoid Tumor (Gastrointestinal), Childhood Carcinoid Tumors, Carcinoma of Unknown Primary, Cardiac (Heart) Tumors, Central Nervous System, Childhood Atypical Teratoid/Rhabdoid Tumor, Childhood Embryonal Tumors, Childhood Germ Cell Tumor, Primary CNS Lymphoma, Cervical Cancer, Childhood Cervical Cancer, Cholangiocarcinoma, Chordoma, Childhood, Chronic Lymphocytic Leukemia (CLL), Chronic Myelogenous Leukemia (CML), Chronic Myeloproliferative Neoplasms, Colorectal Cancer, Childhood Colorectal Cancer, Childhood Craniopharyngioma, Cutaneous T-Cell Lymphoma, Ductal Carcinoma In Situ (DCIS), Embryonal Tumors, Endometrial Cancer (Uterine Cancer), Childhood Ependymoma, Esophageal Cancer, Childhood Esophageal Cancer, Esthesioneuroblastoma, Ewing Sarcoma (Bone Cancer), Childhood Extracranial Germ Cell Tumor, Extragonadal Germ Cell Tumor, Eye Cancer, Childhood Intraocular Melanoma, Intraocular Melanoma, Retinoblastoma, Fallopian Tube Cancer, Fibrous Histiocytoma of Bone (Malignant, and Osteosarcoma), Gallbladder Cancer, Gastric (Stomach) Cancer, Childhood Gastric (Stomach) Cancer, Gastrointestinal Carcinoid Tumor, Gastrointestinal Stromal Tumors (GIST) (Soft Tissue Sarcoma), Childhood Gastrointestinal Stromal Tumors, Germ Cell Tumors, Childhood Central Nervous System Germ Cell Tumors (Brain Cancer), Childhood Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Childhood Head and Neck Cancers, Childhood Heart Tumors, Hepatocellular (Liver) Cancer, Langerhans Cell Histiocytosis, Hodgkin Lymphoma, Hypopharyngeal Cancer (Head and Neck Cancer), Intraocular Melanoma, Childhood Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Childhood Laryngeal Cancer, Papillomatosis, Leukemia, Lip and Oral Cavity Cancer (Head and Neck Cancer), Liver Cancer, Lung Cancer (Non-Small Cell and Small Cell), Childhood Lung Cancer, Lymphoma, Male Breast Cancer, Malignant Fibrous Histiocytoma of Bone and Osteosarcoma, Melanoma, Childhood Melanoma, Intraocular (Eye) Melanoma, Childhood Intraocular Melanoma, Merkel Cell Carcinoma (Skin Cancer), Malignant Mesothelioma, Childhood Mesothelioma, Metastatic Squamous Neck Cancer with Occult Primary (Head and Neck Cancer), Midline Tract Carcinoma Involving NUT Gene, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, Chronic (CML), Myeloid Leukemia, Acute (AML), Chronic Myeloproliferative Neoplasms, Nasal Cavity and Paranasal Sinus Cancer (Head and Neck Cancer), Nasopharyngeal Cancer (Head and Neck Cancer), Childhood Nasopharyngeal Cancer, Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Childhood Oral Cavity Cancer, Osteosarcoma and Malignant Fibrous Histiocytoma of Bone, Ovarian Cancer, Childhood Ovarian Cancer, Pancreatic Cancer, Childhood Pancreatic Cancer, Pancreatic Neuroendocrine Tumors (Islet Cell Tumors), Papillomatosis, Paraganglioma, Childhood Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Childhood Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Childhood Rhabdomyosarcoma (Soft Tissue Sarcoma), Salivary Gland Cancer (Head and Neck Cancer), Childhood Salivary Gland Tumors, Sarcoma, Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Uterine Sarcoma, Sézary Syndrome (Lymphoma), Skin Cancer, Childhood Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, Childhood Stomach (Gastric) Cancer, T-Cell Lymphoma, Cutaneous, Testicular Cancer, Childhood Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Childhood Thyroid Tumors, Transitional Cell Cancer of the Renal Pelvis and Ureter (Kidney (Renal Cell) Cancer), Carcinoma of Unknown Primary, Childhood Cancer of Unknown Primary, Unusual Cancers of Childhood, Ureter and Renal Pelvis, Transitional Cell Cancer (Kidney (Renal Cell) Cancer), Urethral Cancer, Endometrial Uterine Cancer, Uterine Sarcoma, Vaginal Cancer, Childhood Vaginal Cancer, Vascular Tumors (Soft Tissue Sarcoma), Vulvar Cancer, and Wilms Tumor.

The pharmaceutically acceptable compositions of this invention can be administered to humans and other animals orally, rectally, parenterally, intracistemally, intravaginally, intraperitoneally, topically (as by powders, ointments, drops or patch), bucally, as an oral or nasal spray, or the like. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The activity of a compound utilized in this invention as an anti-cancer agent may be assayed according to methods described generally in the art and in the Examples herein.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

EXAMPLES

Example 1: Preliminary Study to Provide Evidence of Pair Production 2 plastic tubes, one containing 50 ml of water and the other containing 25 g of sodium phosphotungstate ($W_{12}Na_3PO_{40}$) dissolved in 50 ml of water were produced. Each tube was irradiated with 6 MV and 18 MV photons.

Figure 1B:
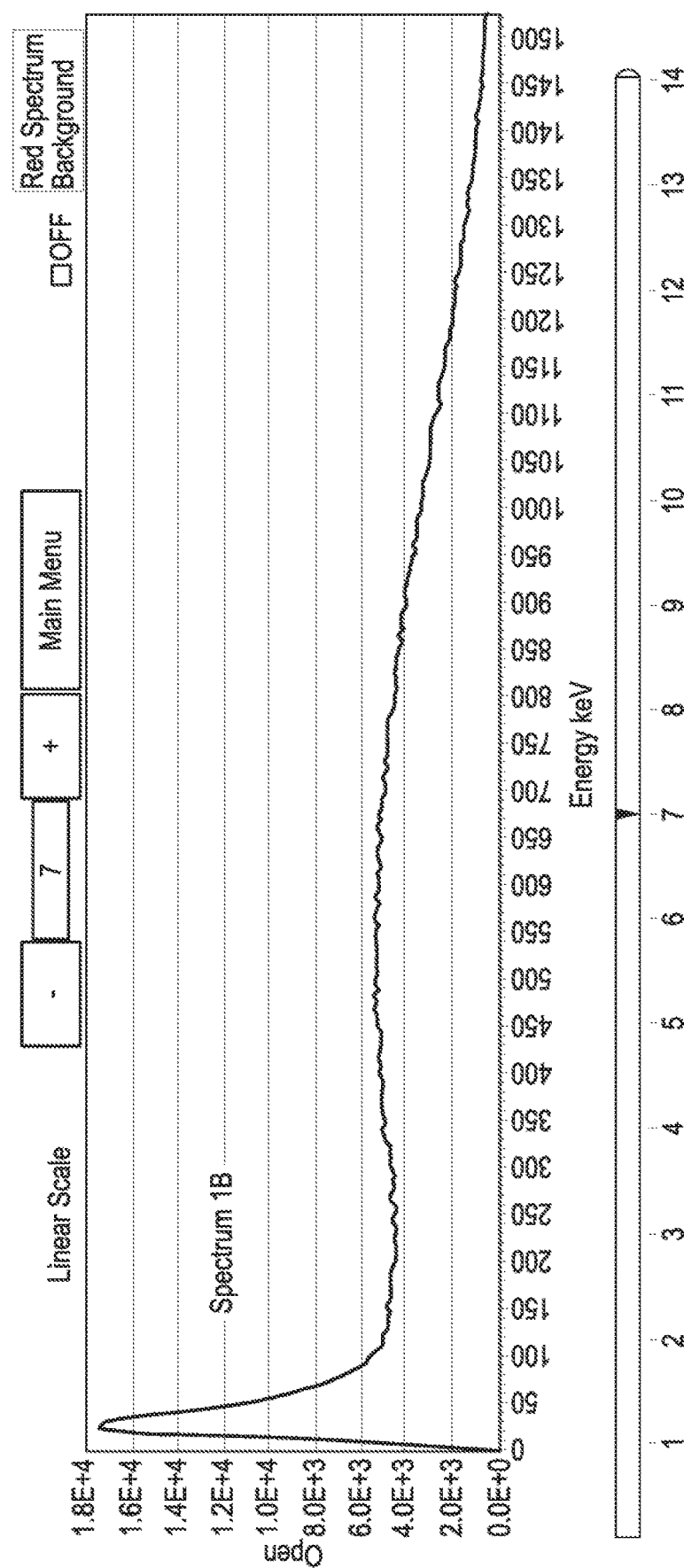
FIG. 1B is a graph of the output of a scintillation detector showing increased emission of photons around 511 keV and higher, signifying pair-production as a 50 mL water sample containing 25 g sodium phosphotungstate is irradiated with 18 MV photons.

The resulting emission spectra were measured with a multi-channel analyzer scintillation detector at approximately 45 degrees oblique from the incident X-ray beam. The spectra at 6 MV were nearly identical with or without dissolved metal, as was the 18 MV spectra with no metal. The emission spectra from the tube containing metal and irradiated with 18 MV photons showed significant increase in photons emitted at 511 keV, signifying the creation and annihilation of positron-electron pairs in situ. The spectra for this experiment are shown in FIG. 1.

Example 2: In Vitro Irradiation of A549 Human Lung Cancer Cells in the Presence of Tungsten or Cisplatin with Varying Levels of High Energy Radiation Detailed Methods: The human lung cancer cell line A549 was maintained in tissue culture using standard techniques. A 70% confluent T25 tissue culture flask of A549 in exponential growth phase was trypsinized with 2 mL of 0.05% trypsin solution and deactivated with 3 mL DMEM to produce a 5 mL single cell-suspension. One milliliter of this cell solution was added to 10 mL of DMEM and vortexed to produce a homogenous diluted single cell suspension. Seven 6-well tissue culture plates were prepared with 3 mL of DMEM per well. Twenty microliters of the A549 cell solution was pipetted into each well of five 6-well plates (approximately 250 cells for the two tungsten experiments and control plates) and the remaining two plates received 80 µL (1000 cells for the following cisplatin experiment as cisplatin alone is cytotoxic). These plates were incubated at 37° C. for 24 hours to allow the cells to settle and the tissue culture wells. The media was then removed from each plate and replaced with: DMEM in 3 plates as non-metal controls (250 cells per well), 100 µM sodium phosphotungstate hydrate DMEM in 2 plates (250 cells per well), 1 mM sodium tungstate dihydrate DMEM in 2 plates (250 cells per well), and 4 µg/mL cisplatin DMEM in 2 plates (1000 cells per well). The media with or without metal compounds was left in the wells to incubate for 1-2 hours prior to irradiation. Six plates were irradiated using a linear accelerator (Varian Trilogy; Varian Corp., Palo Alto, Calif.): one plate each of the DMEM, sodium phosphotungstate hydrate, sodium tungstate dihydrate, and cisplatin were given 209 MU of 6 MV X-rays (2 Gy) and the remaining plates of DMEM, sodium phosphotungstate hydrate, sodium tungstate dihydrate, and cisplatin were irradiated with 239 MU of 18 MV X-rays (2 Gy). The remaining seventh plate was not irradiated and used to calculate plating efficiency of A549. The seven plates then had all media replaced with normal DMEM immediately following irradiation and were incubated for 10 days. When A549 colonies were seen to be equal to or greater than 50 cells by microscopy, the seven plates were stained with crystal violet and counted. The same experiment above was conducted for A549 cells in DMEM media alone with administration of sodium phosphotungstate hydrate after irradiation. Two identical plates were prepared as described above and these were irradiated at 6 or 18 MV in DMEM. The media was removed after irradiation and replaced with 100 µM sodium phosphotungstate hydrate media for one hour before again being replaced with DMEM and incubated for 10 days.

Results: The non-irradiated, non-metal plate was counted first and found to have an average of 102 cells per well, an approximate plating efficiency of 41%. The two plates that were irradiated with DMEM and no metal were then counted and considered to be non-metal controls. The 6 MV irradiated plate showed an average of 66 colonies (64% survival) and the 18 MV irradiated plates showed an average of 69 colonies (67% survival). This confirmed a similar absorbed dose of radiation at either 6 MV or 18 MV. The 6 MV 100 µM sodium phosphotungstate hydrate plates showed an average of 68 colonies (66% survival) while the 18 MV irradiated plates showed an average of 35 colonies (34% survival, approximately double cell kill compared to 6 MV). The 6 MV 1 mM sodium tungstate dihydrate plates showed an average of 70 colonies (68% survival) while the 18 MV irradiated plates showed an average of 21 colonies (20% survival, approximately 70% more cell killing compared to 6 MV). The 6 MV 4 µg/mL cisplatin plate showed an average of 54 colonies (13% survival, lower than previous numbers due to cytotoxicity of cisplatin) and the 18 MV irradiated plates showed an average of 29 colonies (7% survival, approximately half of that at 6 MV). The plates that were exposed to tungsten after irradiation showed similar cell killing to non-metal irradiated controls, approximately 65% at either 6 or 18 MV.

Conclusion: In the absence of metal, 2 Gy of 6 MV and 18 MV irradiation produced nearly identical clonogenic survival of A549 cells, confirming the absorbed dose of radiation is similar between the two energies when linear accelerator output factors are taken into account. When either tungsten or platinum metals were present and 6 MV irradiation was used, no significant change in clonogenic survival was found. When irradiated with 18 MV, both sodium phosphotungstate hydrate and cisplatin plates showed approximately 50% decreased clonogenic survival compared to the 6 MV plates. Sodium tungstate dihydrate showed nearly 70% decreased clonogenic survival at 18 MV vs 6 MV irradiation. Addition of metal after irradiation was completed did not change the clonogenic survival compared to irradiation alone. This effect is due to increased photon-matter interactions in solution, attributable to pair-production, and requires the metal to be present at time of irradiation.

Accordingly, evidence of pair production in the presence of heavy metal and 18 MV photon energy was measured using a scintillation detector and multi-channel analyzer. Pair production using 18 MV photons was not evident in the absence of heavy metal. Pair production was not evident using 6 MV photon energy in the presence of heavy metal.

Further, enhanced cytotoxicity was demonstrated experimentally in vitro using clonogenic survival assays in the presence of heavy metal and 18 MV photon energies. Enhanced cytotoxicity using 18 MV photons was not evident in the absence of heavy metal. Enhanced cytotoxicity was not evident using 6 MV photon energy in the presence of heavy metal.

Example 3: In Vitro Irradiation of A549 Human Lung Cancer Cells in the Presence of Tungsten, Carboplatin, or Cisplatin with Varying Levels of High Energy Radiation A549 lung cancer cells were used to create nine 6-well plates under standard methods. The media was then removed from each plate and replaced with: DMEM in 3 plates as non-metal controls (250 cells per well), 100 µM sodium phosphotungstate hydrate DMEM in 2 plates (250 cells per well), 12 µg/ml carboplatin DMEM in 2 plates (1000 cells per well), and 4 µg/ml cisplatin DMEM in 2 plates (1000 cells per well) and incubated for 2-4 hours prior to irradiation. Eight plates were irradiated on a linear accelerator: one plate each of the DMEM, tungsten, carboplatin, and cisplatin was given 2 Gy of 6 MV X-rays and one of each was irradiated with 2 Gy of 18 MV X-rays. The remaining plate was not irradiated and used to calculate plating efficiency of A549. The nine plates were incubated for 10 days, stained with crystal violet, and colonies were counted.

Results: The 6 MV plate with no metal (M–) grew 66 colonies/well (64% survival) and the 18 MV M– plate grew 69 colonies/well (67% survival). The 6 MV 100 µM tungsten plate grew 68 colonies/well (66% survival) while the 18 MV plate containing tungsten grew 35 colonies/well (34% survival). The 6 MV cisplatin plate grew 54 colonies/well (13% survival) and the 18 MV cisplatin plate grew 29 colonies/well (7% survival). The 6 MV 12 µg/ml carboplatin plate grew 64 colonies/well (16% survival) and the 18 MV irradiated plate grew 40 colonies/well (10% survival).

Conclusion: Cells receiving 18 MV X-rays with tungsten metal showed approximately 50% more cell killing compared to 6 MV+/– M and 18 MV –M. Cisplatin and carboplatin show 37% more cell killing at 18 MV vs 6 MV. This effect is attributable to increased pair-production.

Example 4: Dose Response Curve of In Vitro Experiments Using A549 Cells

Figure 2:
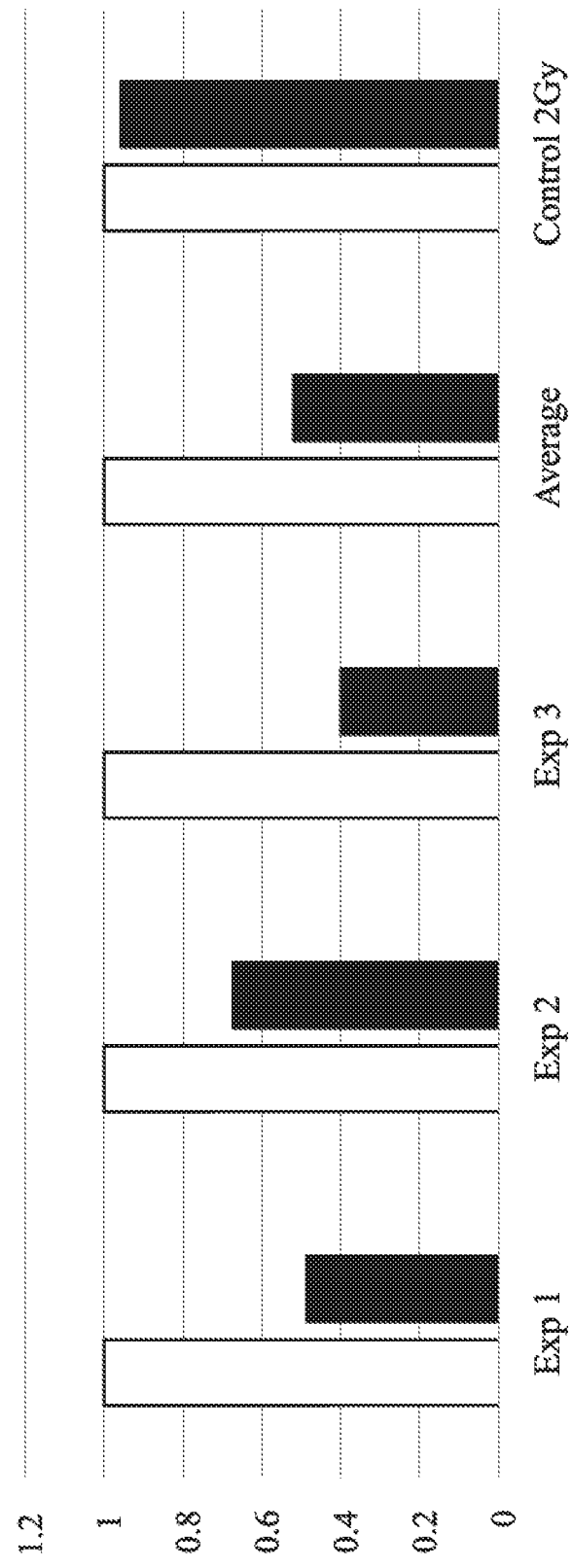
FIG. 2 is a bar graph showing 3 experiments using A549 lung cancer cells exposed to 100 µM sodium phosphotungstate for 2 hours before irradiation with 2 Gy of 6 MV or 18 MV photons. Data is normalized so that 6 MV survival is 1 for each experiment. The average of 3 experiments showed cell survival was decreased by 48% when using 18 MV photons compared to 6 MV photons. Control experiment using 6 MV vs 18 MV photons without metal drug added before irradiation shows nearly identical cell survival, confirming similar absorbed dose at different energies.

In vitro studies were conducted with the A549 cell line, a human lung adenocarcinoma cultured from the tumor of a 58 y/o Caucasian male by Giard in 1972. Clonogenic survival studies were done without irradiation or metal compound to measure plating efficiency. Cells were then exposed to 100 µM tungsten compound for 4 hours and seeded into 6 well plates. Survival was found to be greater than 95% after drug administration without irradiation, suggesting low toxicity of metal drug. 4 identical plates of cells were then created, 2 containing 100 µM tungsten metal and 2 without metal. One of each plate was irradiated with 2 Gy of 6 MV photons and the others with 2 Gy of 18 MV (accounting for the difference in depth-dose between 6 and 18 MV). The culture media of each plate was exchanged with metal-free media after irradiation and the plates were incubated for 10 days before colonies were counted. The plate of cells containing tungsten metal and irradiated with 18 MV photons showed approximately 50% more cell killing compared to 6 MV with or without metal and 18 MV without metal. Cell survival was compared between 2 Gy, 6 MV (209 MU) and 2 Gy, 18 MV (239 MU) to ensure that the same absorbed dose of radiation was given (FIG. 2). The results of additional similar experiments with Tungsten are provided in FIGS. 5-9.

Figure 3:
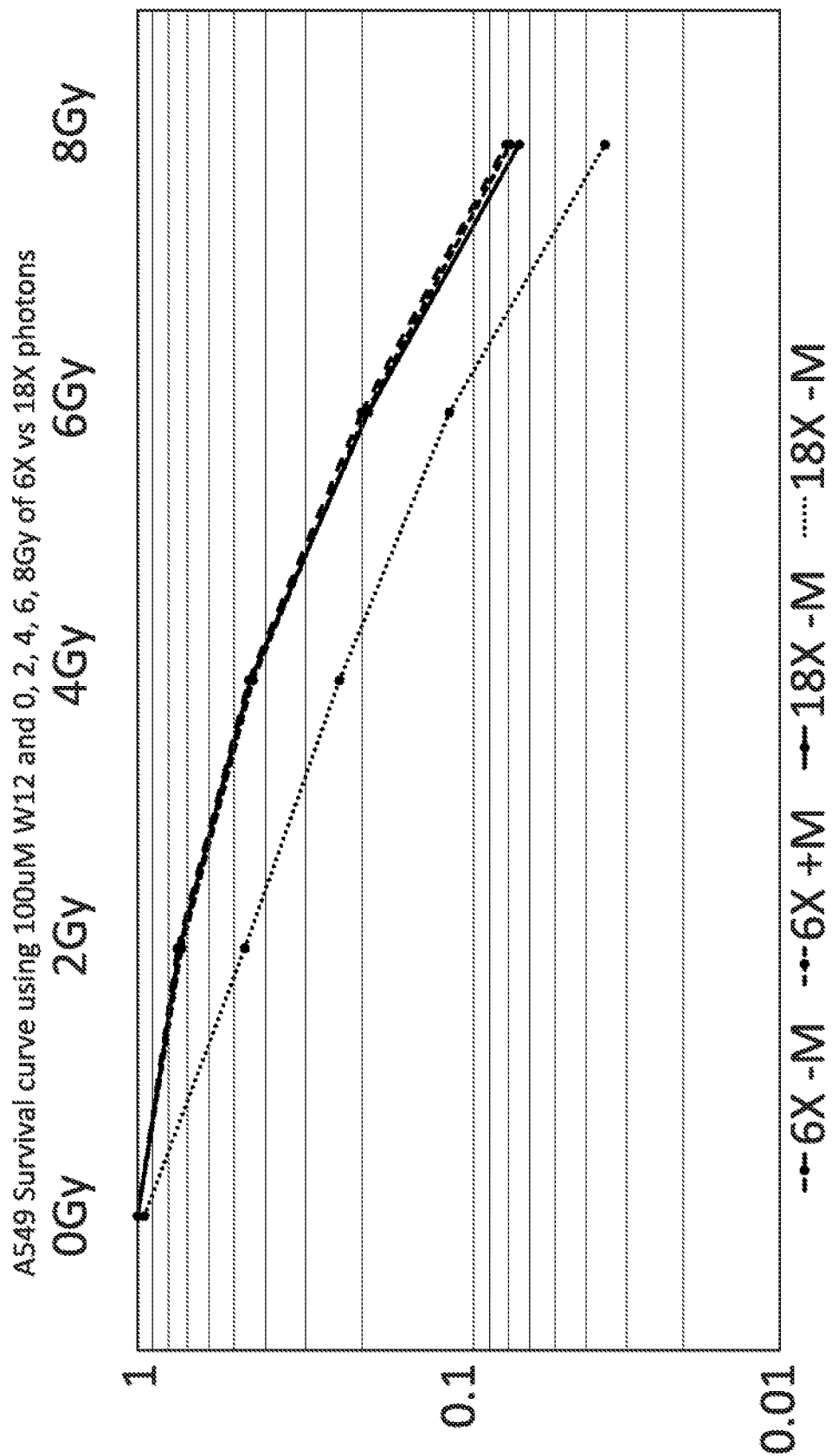
FIG. 3 is a line graph of the cell survival curve generated with A549 cells, with and without metal drug added 2 hours before exposure to either 6 MV or 18 MV irradiation at 0, 2, 4, 6, and 8 Gy. The curves for 6 MV no metal, 18 MV no metal, and 6 MV with metal are nearly identical, while the 18 MV with metal curve is significantly shifted. The loss of shoulder suggests decreased DNA repair.

A dose response curve was then generated by the same methods as above at 0, 2, 4, 6, and 8 Gy of radiation (FIG. 3). The sensitization enhancement ratio (SER) was found to be between 1.3 and 1.5. This dose response curve shows abolishment of the low dose shoulder region (exactly what you would expect from high LET radiation), indicating that DNA damage is unrepairable when high energy photons interact with metal complexes.

Figure 4:
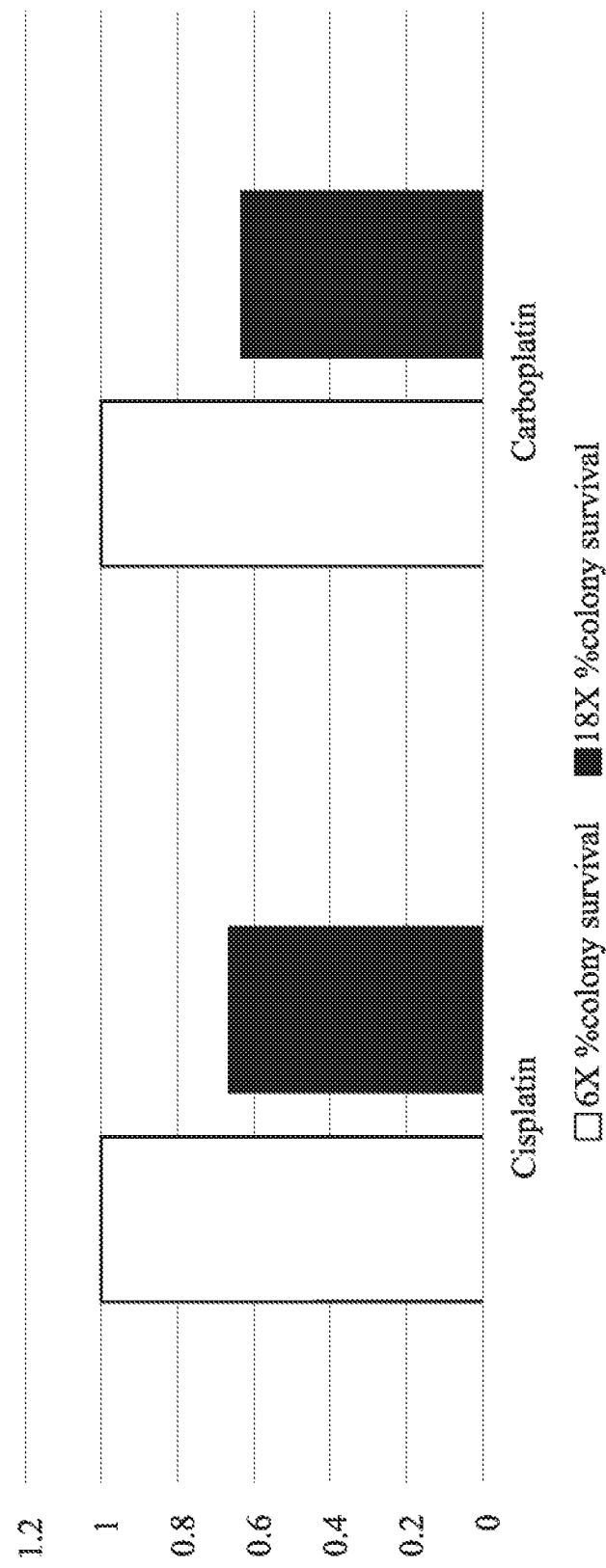
FIG. 4 is a bar graph showing the cell survival of A549 lung cancer cells exposed to 4 µg/ml cisplatin and 12 µg/ml carboplatin 2 hours before irradiation with 2 Gy of 6 MV or 18 MV photons. Data is normalized so that 6 MV survival is 1 for each experiment. The average of 3 experiments showed cell survival was decreased by approximately 37% for both drugs when using 18 MV photons compared to 6 MV photons.
Figure 5:
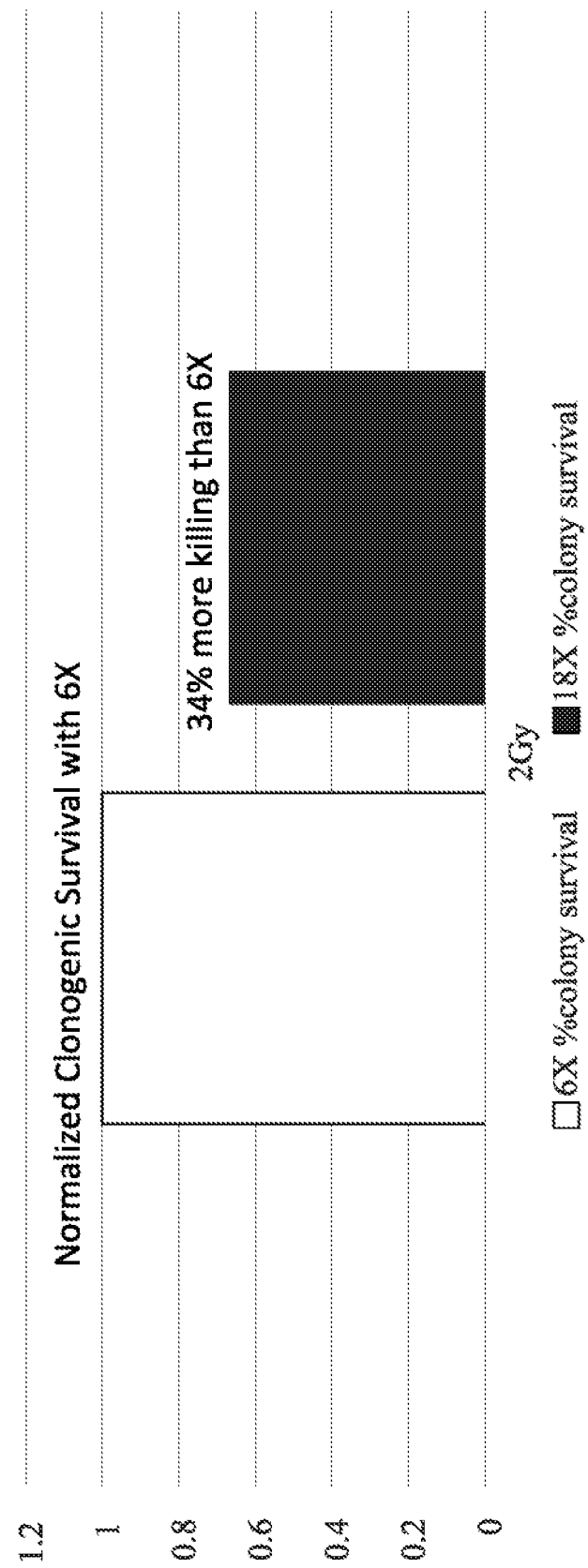
FIG. 5 is a bar graph providing additional cell kill at equidose (i.e. 2 Gy) for 18 MV and 6 MV photons in the presence of heavy metal, platinum bound as carboplatin.
Figure 6:
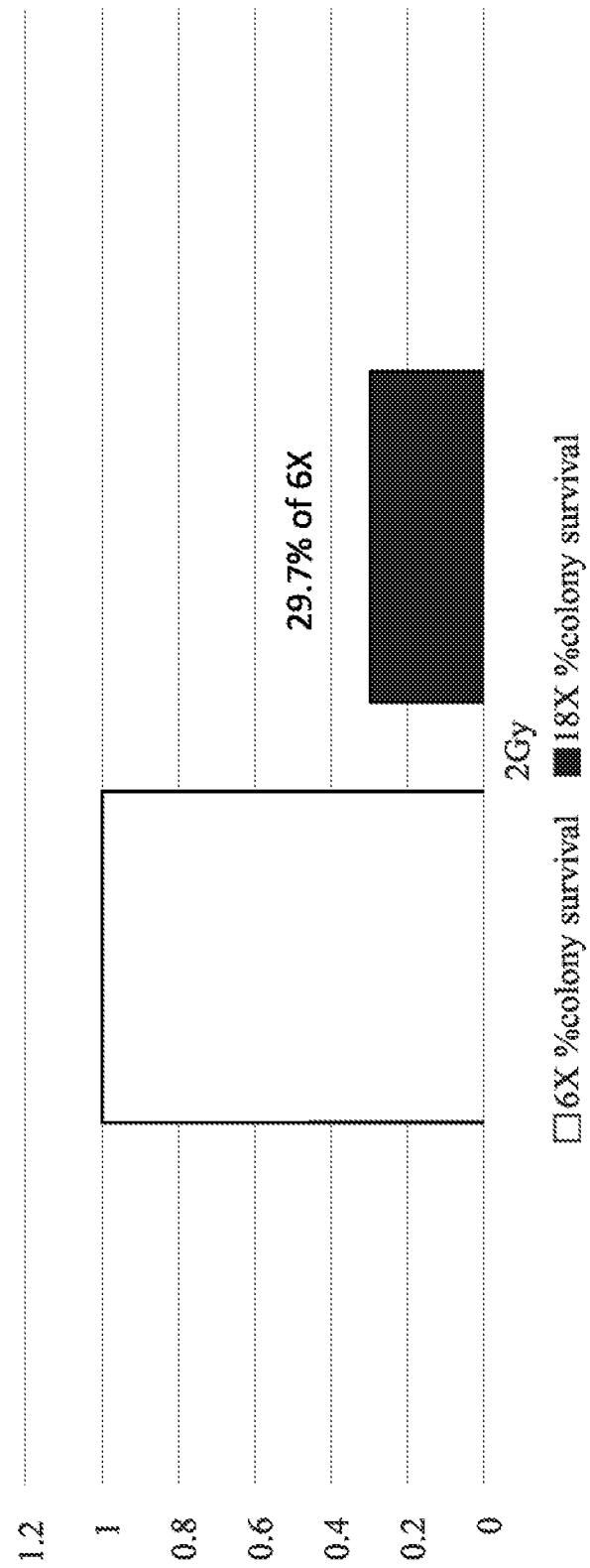
FIG. 6 is a bar graph providing additional cell kill at equidose (i.e. 2 Gy) for 18 MV and 6 MV photons in the presence of heavy metal, Tungsten bound as $Na_2WO_4(H_2O)_2$.
Figure 7:
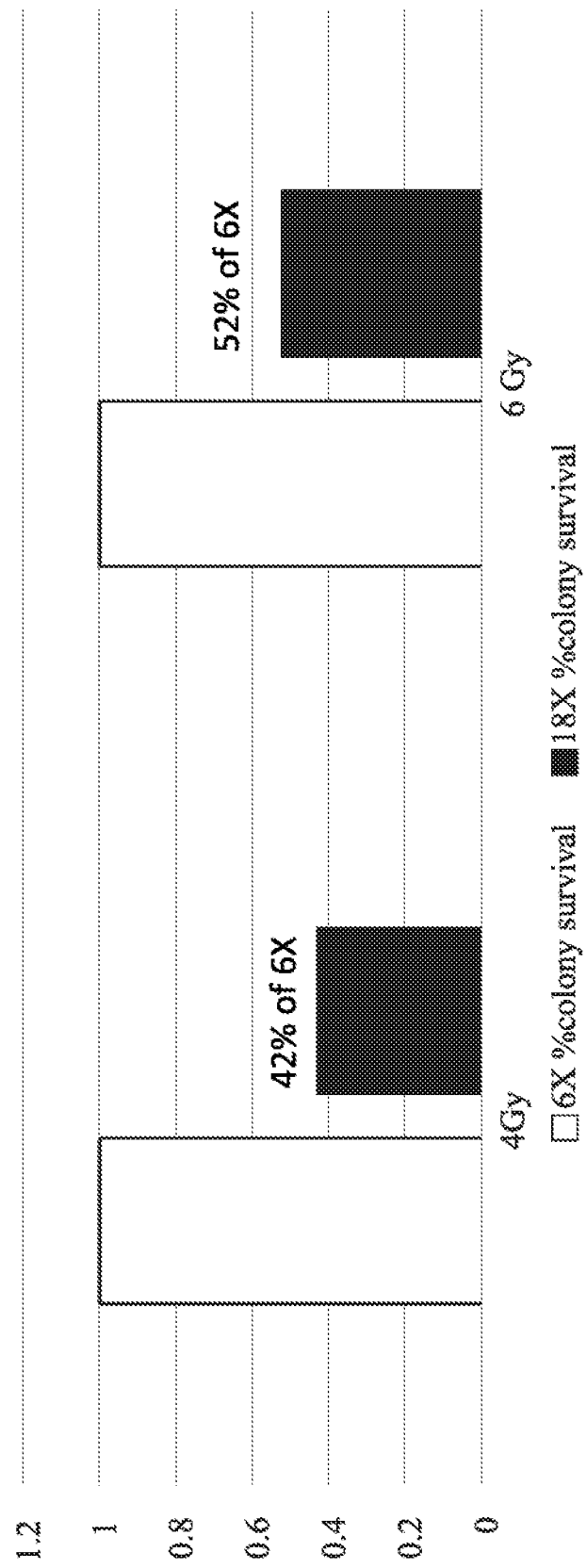
FIG. 7 is a bar graph providing additional cell kill at equidose (i.e. 4 and 6 Gy) for 18 MV and 6 MV photons in the presence of heavy metal, Tungsten.
Figure 8:
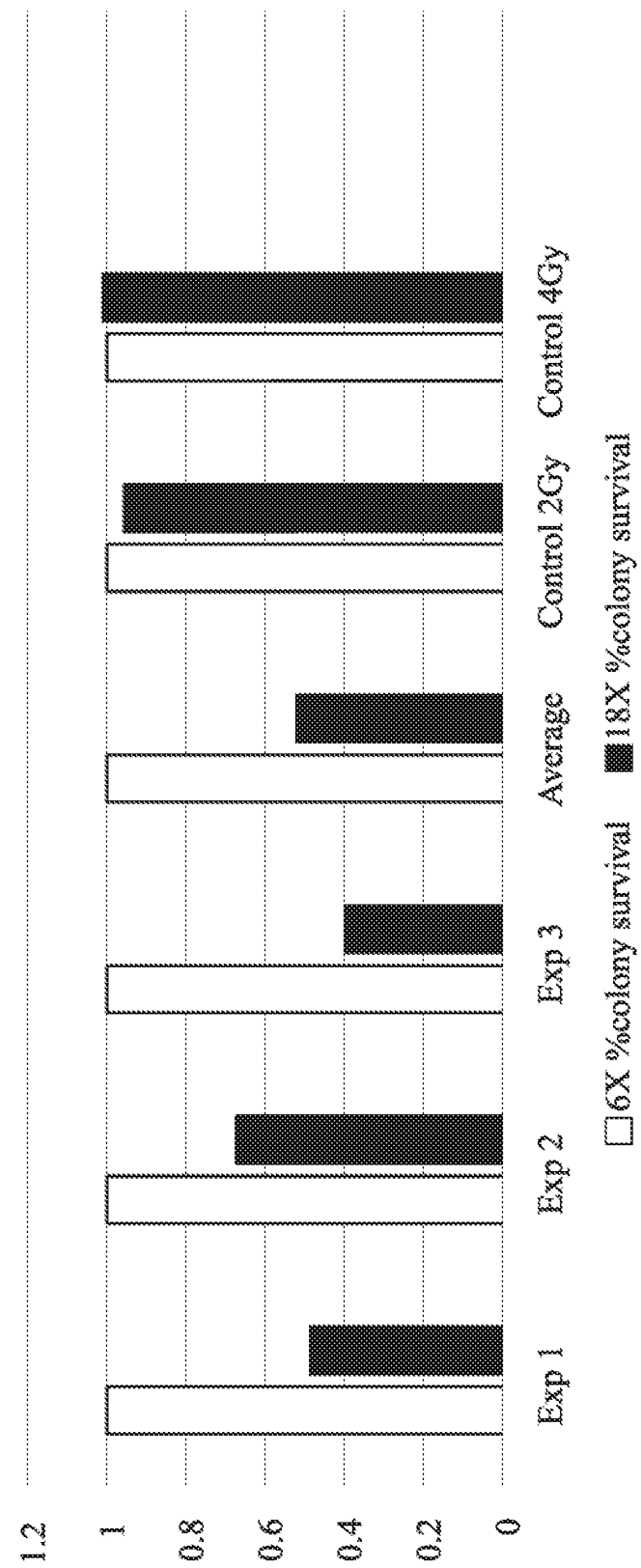
FIG. 8 is a bar graph providing additional cell kill at equidose (i.e. 2 and 4 Gy) for 18 MV and 6 MV photons in the presence of heavy metal, Tungsten.
Figure 9:
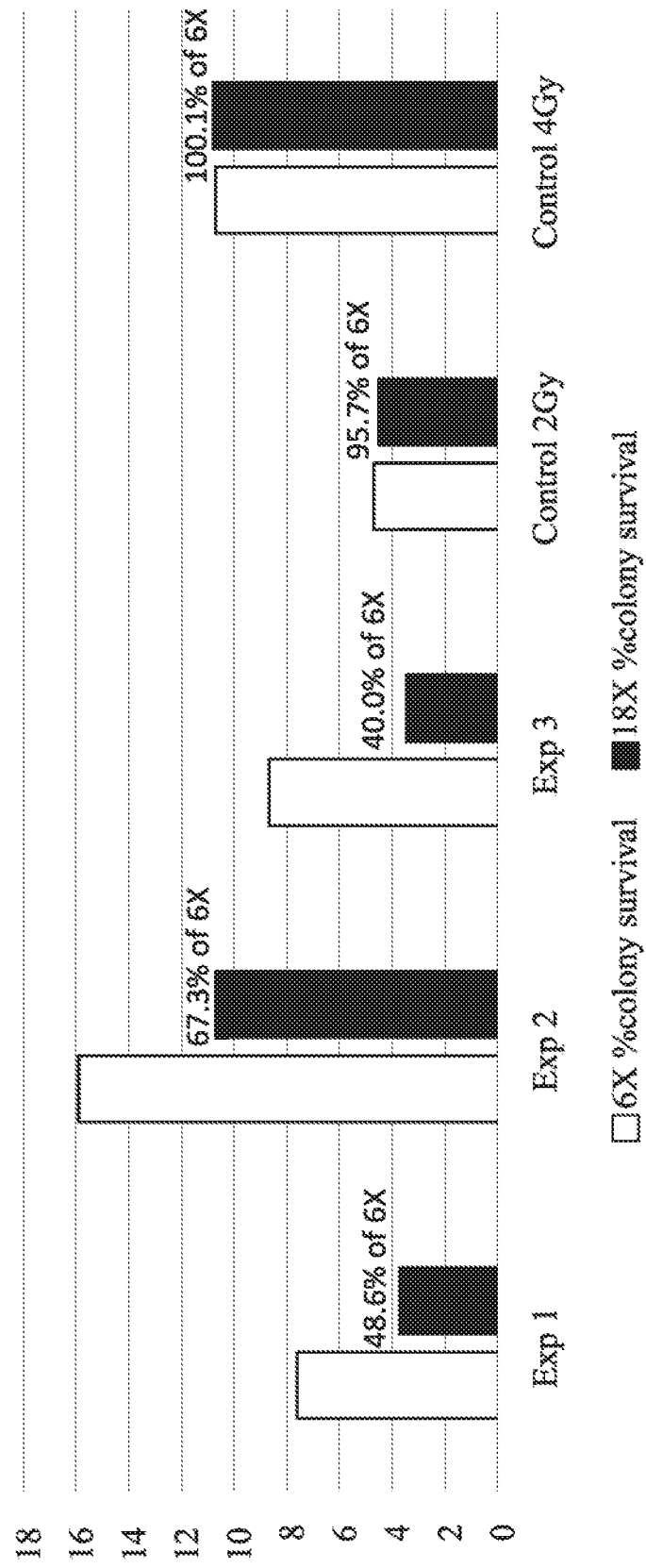
FIG. 9 is a bar graph providing additional cell kill at equidose (i.e. 2 and 4 Gy) for 18 MV and 6 MV photons in the presence of heavy metal, Tungsten.

In vitro studies were conducted similarly to above with both cisplatin (4 µg/ml) and carboplatin (12 µg/ml). These compounds showed radiosensitization at 18 MV compared to 6 MV, resulting in increased cell killing of, on average, approximately 37% (FIG. 4).

Other heavy metal drugs such as gold compounds and other high Z organometallic compounds, as well as an array of nanoparticles containing tungsten, gold, and platinum are believed to exhibit pair-production generation in situ. The amount of pair-production generated from each metal compound will be quantified using a multichannel analyzer/scintillation detector, Gafchromic film and/or a simplified portable PET scanner used in conjunction with the clinical linear accelerator.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims.

What is claimed is:

1. A method of treating a solid-tumor selected from the group consisting of a Childhood Lung Cancer, a Non-Small Cell Lung Cancer, and a Small Cell Lung Cancer in a patient, wherein the patient is a mammal, comprising the steps of:
   a. administering to the patient a pharmaceutically acceptable composition comprising a heavy metal organometallic compound;
   b. allowing a time interval of 5 minutes to 12 hours to pass; and
   c. irradiating the area of the patient previously identified as the location of the solid tumor with a dose of high energy photons having an energy of 15 MV to 50 MV sufficient to induce positron-electron pair production at the site of the solid tumor.

2. The method of claim 1, wherein the patient is a human.

3. The method of claim 1, wherein the treatment includes killing cells of the solid tumor.

4. The method of claim 1, wherein the heavy metal organometallic compound comprises one or more of tungsten, platinum, gold, mercury, cadmium, arsenic, chromium, thallium, and lead.

5. The method of claim 1, wherein the heavy metal organometallic compound comprises a metal having low toxicity.

6. The method of claim 1, wherein the heavy metal organometallic compound comprises tungsten.

7. The method of claim 1, wherein the dose of high energy photons is from 2 Gr to 20 Gr.

* * * * *